United States Patent
Tschirren et al.

(10) Patent No.: US 12,186,542 B2
(45) Date of Patent: Jan. 7, 2025

(54) DETACHABLE NEEDLE PROTECTION CAP FOR INJECTION DEVICES

(71) Applicant: Ypsomed AG, Burgdorf (CH)

(72) Inventors: Markus Tschirren, Burgdorf (CH); Ulrich Moser, Heimiswil (CH); Marc Fiechter, Konolfingen (CH); Urs Kloetzli, Burgdorf (CH); Felix Groetzbach, Gerlafingen (CH)

(73) Assignee: Ypsomed AG, Burgdorf (CH)

( * ) Notice: Subject to any disclaimer, the term of this patent is extended or adjusted under 35 U.S.C. 154(b) by 166 days.

(21) Appl. No.: 17/700,719

(22) Filed: Mar. 22, 2022

(65) Prior Publication Data
US 2022/0211950 A1 Jul. 7, 2022

Related U.S. Application Data

(60) Division of application No. 16/353,805, filed on Mar. 14, 2019, now Pat. No. 11,331,437, which is a
(Continued)

(30) Foreign Application Priority Data

Sep. 21, 2016 (CH) ........................................ 1224/16

(51) Int. Cl.
*A61M 5/32* (2006.01)
*A61M 5/20* (2006.01)
*A61M 5/50* (2006.01)

(52) U.S. Cl.
CPC ............ *A61M 5/3202* (2013.01); *A61M 5/20* (2013.01); *A61M 5/2033* (2013.01);
(Continued)

(58) Field of Classification Search
CPC .... A61M 5/20; A61M 5/3202; A61M 5/3245; A61M 5/326; A61M 5/5086; A61M 2005/2073; A61M 2005/3254
See application file for complete search history.

(56) References Cited

U.S. PATENT DOCUMENTS

| 4,372,593 A | 2/1983 | Kesselman |
| 2010/0185178 A1* | 7/2010 | Sharp .................. A61M 5/3129 604/110 |

(Continued)

FOREIGN PATENT DOCUMENTS

| CH | 711142 A2 | 11/2016 |
| EP | 2745866 B1 | 10/2016 |

(Continued)

OTHER PUBLICATIONS

PCT, "International Report on Patentability", Application No. PCT/CH2017/00081, Mar. 26, 2019, 12 pages.
(Continued)

*Primary Examiner* — Robert J Utama
*Assistant Examiner* — Justin L Zamory
(74) *Attorney, Agent, or Firm* — Dorsey & Whitney LLP

(57) ABSTRACT

The invention relates to a detachable needle protection cap for injection devices and to a method for producing same. The detachable needle protection cap comprises a housing and at least two shell parts which can be attached to an outer surface of the housing, the shell parts being fastened to an outer surface of the housing. The shell parts can mutually prevent removal of the shell parts.

8 Claims, 5 Drawing Sheets

Related U.S. Application Data continuation of application No. PCT/CH2017/000081, filed on Sep. 6, 2017.

(52) U.S. Cl.
CPC ........ *A61M 5/3204* (2013.01); *A61M 5/3245* (2013.01); *A61M 5/5086* (2013.01); *A61M 2005/2073* (2013.01); *A61M 2005/3254* (2013.01); *A61M 5/326* (2013.01)

(56) References Cited

U.S. PATENT DOCUMENTS

| | | |
|---|---|---|
| 2010/0286620 A1 | 11/2010 | Edginton et al. |
| 2012/0029439 A1 | 2/2012 | Hudson et al. |
| 2014/0364804 A1 | 12/2014 | Stillson |
| 2019/0209786 A1 | 7/2019 | Tschirren et al. |

FOREIGN PATENT DOCUMENTS

| | | |
|---|---|---|
| GB | 2100380 A | 12/1982 |
| WO | 2005110532 A1 | 11/2005 |
| WO | 2014111370 A1 | 7/2014 |
| WO | 2014146209 A1 | 9/2014 |
| WO | 2016205961 A8 | 2/2018 |
| WO | 2018053657 A1 | 3/2018 |

OTHER PUBLICATIONS

PCT, "International Search Report and Written Opinion", Application No. PCT/CH2017/000081, Dec. 22, 2017, 15 pages.

\* cited by examiner

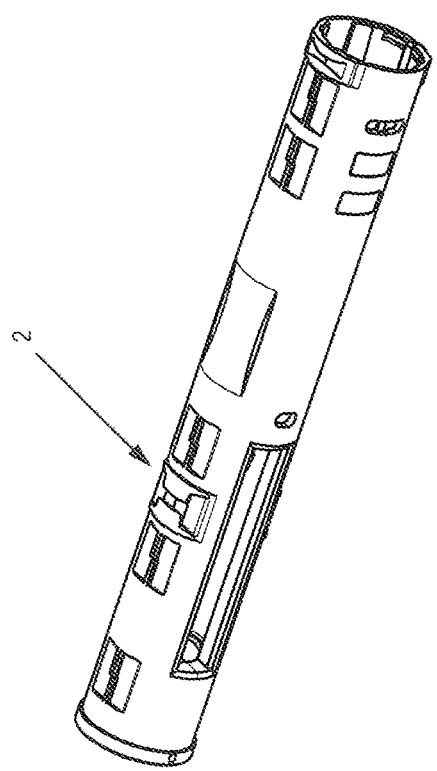
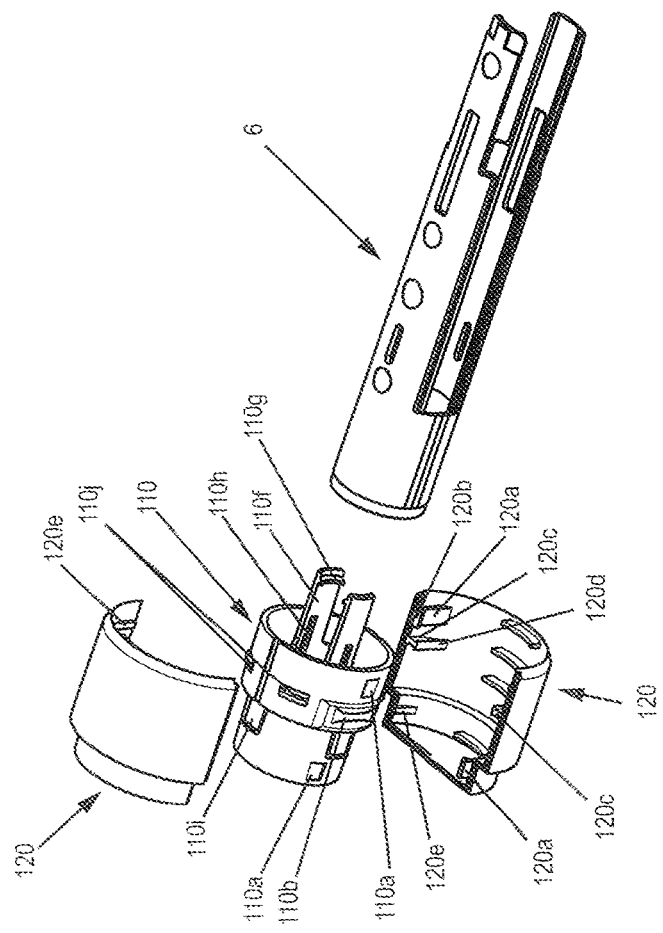
Fig. 2

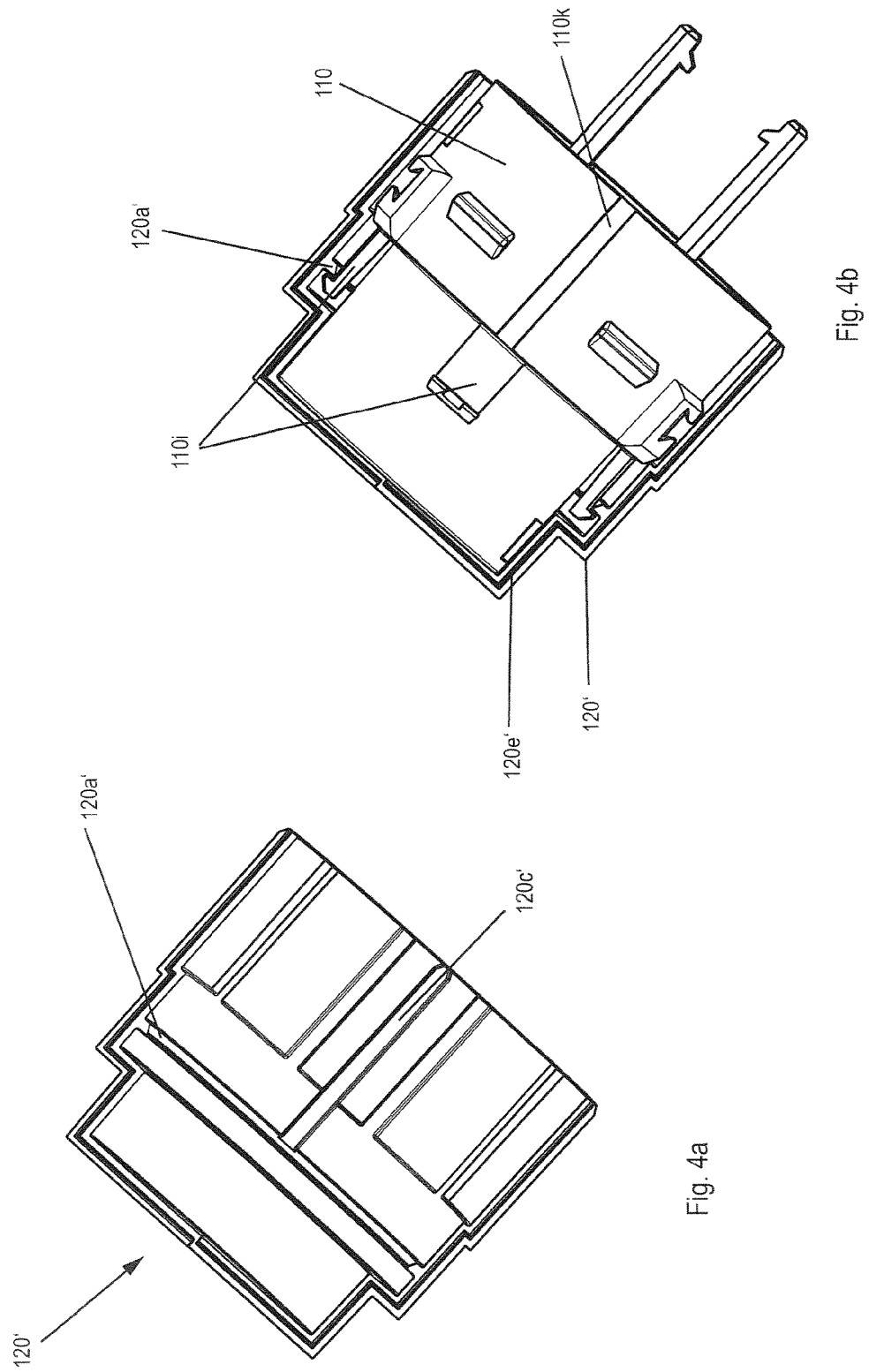

DETACHABLE NEEDLE PROTECTION CAP FOR INJECTION DEVICES

CROSS-REFERENCE TO RELATED APPLICATIONS

This application is a divisional of U.S. patent application Ser. No. 16/353,805 filed on Mar. 14, 2019 which is a continuation of International Application No. PCT/CH2017/000081 filed on Sep. 6, 2017, which claims priority to Swiss Application No. 1224/16 filed Sep. 21, 2016, the entire contents of all of which are incorporated by reference herein in their entirety.

FIELD OF THE INVENTION

The invention relates to detachable needle protection caps for injection devices, in particular for injection pens and autoinjectors, in which pre-filled syringes are used as product containers and with which a liquid product contained therein can be dispensed. The liquid product in question is a medicinal product in particular. The invention essentially relates to detachable needle protection caps for injection devices, which can be cheaply adapted to the needs of various medical indications.

BACKGROUND

An injection device, such as an injection pen, an autopen or an autoinjector is, in principle, suitable for dispensing various medicaments, provided that the medicament is of a consistency that can be dispensed using the injection device. However, there are differences which are caused indirectly by the medical indications, for which the various medicaments are used. Thus, because of the indication, various demands may be made in terms of size, shape, surface and mechanical properties of the housing of the injection device. For example, in the case of diseases such as multiple sclerosis (MS), the mobility of the patient may be restricted, meaning that for an injection device which is used to treat patients with MS, particular demands are made on the shape of the device, so that the patients can handle the injection device in the first place. Thus, for medical indications which concern the handling of injection devices by children or small people, it may be necessary for injection devices to be designed as slim and small as possible.

For injection devices where a prefilled syringe is used as a product container, a so-called detachable needle protection cap is often used so as to be able to remove the needle protection from the syringe prior to injecting. Using the detachable needle protection cap, the person using the unit can remove the needle protection from the syringe by hand. It is immediately obvious that the shape and design of the detachable needle protection cap must likewise be adapted to the application (as described above).

The term "medicament" in this case includes any fluid medicinal formulation, which is suitable for controlled administration through a means, such as a cannula or hollow needle, for example, including a fluid, a solution, a gel, an emulsion or a fine suspension, which contains one or more active medicinal substances. A "medicament" may be a composition of a single active substance or a premixed or co-formulated composition of several active substances from one single container. Medicament includes drugs such as peptides (e.g. insulins, insulin-containing medicaments, GLP-1-containing as well as derivatives or similar preparations), proteins and hormones, biologically obtained or active substances, active substances based on hormones or genes, nutritional formulations, enzymes and other substances both in solid (suspended) or liquid form, as well as polysaccharides, vaccines, DNA or RNA or oligonucleotides, antibodies or parts of antibodies, as well as suitable base, auxiliary and carrier substances.

An injection device is known from WO 15110532 A1, which comprises a multi-part detachable needle protection cap. The detachable needle protection cap comprises a cap 50 and an insert 90, which are connected by a single snap-on connection. A particular variant, which is designed in one piece, is provided for the cap 50.

For manufacturers of injection devices, drug manufacturers, health insurers and patients, there is a need for injection devices to be readily available, which are as cheap as possible but which are safe and effective. Accordingly, it would be desirable to have a detachable needle protection cap for an injection device, which comprises a consistent, tried and tested, safe and prescribed technical design with a consistent housing, where connection is made by additional components, which are permanently and non-detachably connected to the housing of the injection device as well as connected to the detachable needle protection cap and where the shape, feel, surface topography and ergonomy of the injection device can still be adapted during production of the device, thereby taking account of the needs of the medical indication in a simple and cost-effective way.

The invention provides detachable needle protection caps for injection devices, which can be cost-effectively adapted to the needs of various medical indications.

SUMMARY OF THE INVENTION

Such needle protection caps are provided for instance by the device according to independent claim 1 and the process according to the independent claim 6. Advantageous further developments can be seen from the dependent claims, the description and figures.

In the following description, the terms 'distally' and 'proximally' are used in relation to positions and directions. For example, the distal end of the injection device means the end of the injection device where the injection needle is attached. The distal direction then indicates the direction in which the tip of the injection needle points. In other words, 'proximal' then describes the end opposite the distal end, or the direction which is opposite the distal direction.

The function of the detachable needle protection cap is briefly explained below using an autoinjector in the shape of a pen as an example. However, other injection devices with a detachable needle protection cap according to the invention could also be used if a prefilled syringe is used as the product container in said injection devices. The injection devices may, in particular, also be injection pens or autopens.

Typically, prefilled syringes are used as medicament containers in autoinjectors. An injection needle is permanently attached at the distal end of the syringe. The injection needle is protected, prior to use, by a needle guard in the form of a rubber cap (possibly with a reinforced support frame), where the rubber cap also forms a sterile barrier. When assembling the autoinjector, the prefilled syringe is pushed into the autoinjector, where it is fixed. The distal end of the autoinjector is formed by the detachable needle protection cap, which makes it possible to remove the needle guard from the prefilled syringe before the autoinjector is used, without the person using the syringe running the risk of pricking himself on the injection needle.

In one aspect of the invention, the detachable needle protection cap comprises a housing. The housing together with the autoinjector defines a longitudinal axis and the radii are defined as perpendicular to the longitudinal axis. To detach the needle guard from the prefilled syringe, at least two flexible arms are located on the housing, which point in the proximal direction and the proximal ends of which have hook-like structures, which protrude radially inward behind the proximal end of the needle protection cap when the detachable needle protection cap is placed on the autoinjector. If the detachable needle protection cap is now removed from the autoinjector in the distal direction, then the hook-like structures grip the needle guard and detach it from the prefilled syringe.

In principle, the housing of the needle protection cap is approximately cylindrical in shape and the housing may include areas of different diameters. On the outer surface of the housing of the detachable needle protection cap, additional elements are arranged, which makes it possible to attach and fix additional parts.

In one aspect of the invention, the detachable needle protection cap also comprises at least two shell parts, which can be fitted on the outside of the housing. The shell parts comprise complementary elements, particularly attachment and guide elements which, when engaged with the elements on the outside of the housing, enable the shell parts to be fixed to the housing. Furthermore, the shell parts comprise blocking elements, which can prevent the shell parts from becoming detached after fitting to the housing. According to the invention, the blocking elements of a shell part block the complementary elements from becoming detached from another shell part and vice-versa, which has the advantage that when the at least two shell parts are fixed to the housing, non-destructive detachment of the shell parts is rendered impossible (without parts of the detachable needle protection cap being damaged).

The positioning of the complementary elements and the blocking elements on the shell parts can be seen from the arrangement of the elements on the external surface of the housing.

The at least two shell parts enable the external shape of the detachable needle protection cap to be adapted to specific needs, without having to make modifications to the housing and function of the detachable needle protection cap. No modifications have to be made to the injection device either, provided that the shape and size of the shell parts do not interfere with the injection device. Therefore, when designing the shell parts, particular care must be taken that the complementary elements are positioned geometrically correctly and that they fit the housing. In addition, there are numerous design possibilities of adjusting the ultimate external shape of the detachable needle protection cap to specific needs.

In their entirety, the shell parts can fully envelop the housing (provided it is outside the injection device when assembled)—in this way, the shell parts may, for example, be developed as half shells. As an alternative, the shell parts may also only cover certain areas of the housing.

As mentioned, the interaction between the elements, complementary elements and blocking elements is designed in such a way that once all the shell parts have been fitted to the housing, the shell parts can no longer be removed from the housing, so that the user is unaware of the multiple parts of the detachable needle protection cap. For this purpose it is important that the shell parts can be fitted permanently and immovably relative to the housing.

In one aspect of the invention, the complementary elements of the shell parts comprise snap arms, on the one hand, and the elements on the external surface of the housing comprise recesses, into which the snap arms can be locked. The complementary elements also comprise guide ribs and the elements comprise guide groves, which run roughly perpendicular to the longitudinal axis. The guide grooves comprise undercuts. So that a shell part can be snapped onto the housing, the shell in question is pushed radially onto the housing, so that the guide ribs can be moved into the provided grooves. The cross-section of the guide ribs is such that the ribs engage in the undercuts of the guide grooves. The shell part is slid on so far until the snap arms click into the recesses.

In one aspect of the invention the detachable needle protection cap comprises two shell parts, which are developed as half shells, so that once the first shell part has been pushed onto the housing, the second shell part is pushed onto the side of the housing opposite the first shell part and the guide ribs of the second shell part are likewise pushed into guide grooves. When the snap arms engage in the recesses, the blocking elements of the second shell part block the snap arms of the first shell part and vice-versa. This prevents the shell parts from becoming detached from the housing, as explained below. In one aspect of the invention, the result of the undercuts in the guide grooves of the housing is that the shells can only be moved minimally in the radial direction, in other words, within the limits of play in the guide groove/guide rib joint. Preferably, the guide grooves and guide ribs are combined in a dovetail.

In an alternative embodiment of the invention, the guide grooves may be arranged on the shell parts and the guide ribs on the external surfaces of the housing.

BRIEF DESCRIPTION OF THE DRAWINGS

FIG. 2: simplified exploded view of autoinjector 1 with detachable needle protection cap 100, where only the housing 2 of the autoinjector and the needle protection sleeve 6 of the autoinjector are shown (for reasons of clarity, the other parts of the autoinjector are not shown).

FIG. 4a: three-dimensional or perspective view of an alternative embodiment of a shell part 120'.

FIG. 4b: three-dimensional or perspective view of the alternative shell part 120', placed on the housing 110.

DETAILED DESCRIPTION

The following describes preferred embodiments of the detachable needle protection cap for injection devices, to which the invention could be applied, particularly to autoinjectors. In no way should this description be interpreted in a restrictive way, but should simply highlight possible embodiments. For example, the invention could also be used in other injection devices, such as the Ypsomed ServoPen® or the Novo Nordisk FlexPen®.

The mechanical part of the autoinjector 1 was omitted from the figures for reasons of clarity. The person skilled in the art is aware of well-known mechanisms, for example, from the applications WO2014/146209A1 or PCT/CH2016/000084, which are herein incorporated by reference in their entireties for any useful purpose.

Figure 1:
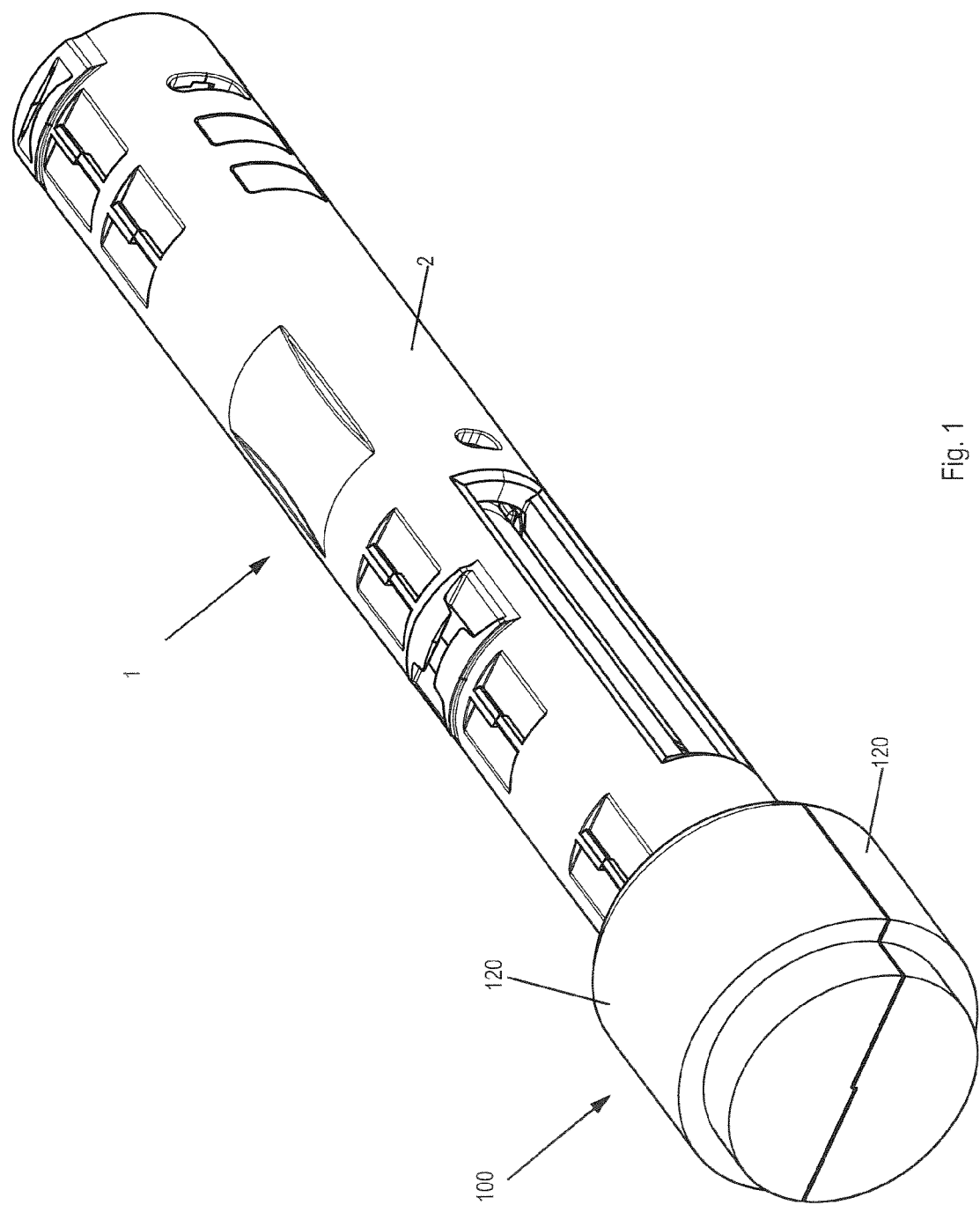
FIG. 1: three-dimensional or perspective view of the autoinjector 1 with the detachable needle protection cap 100.
Figure 3:
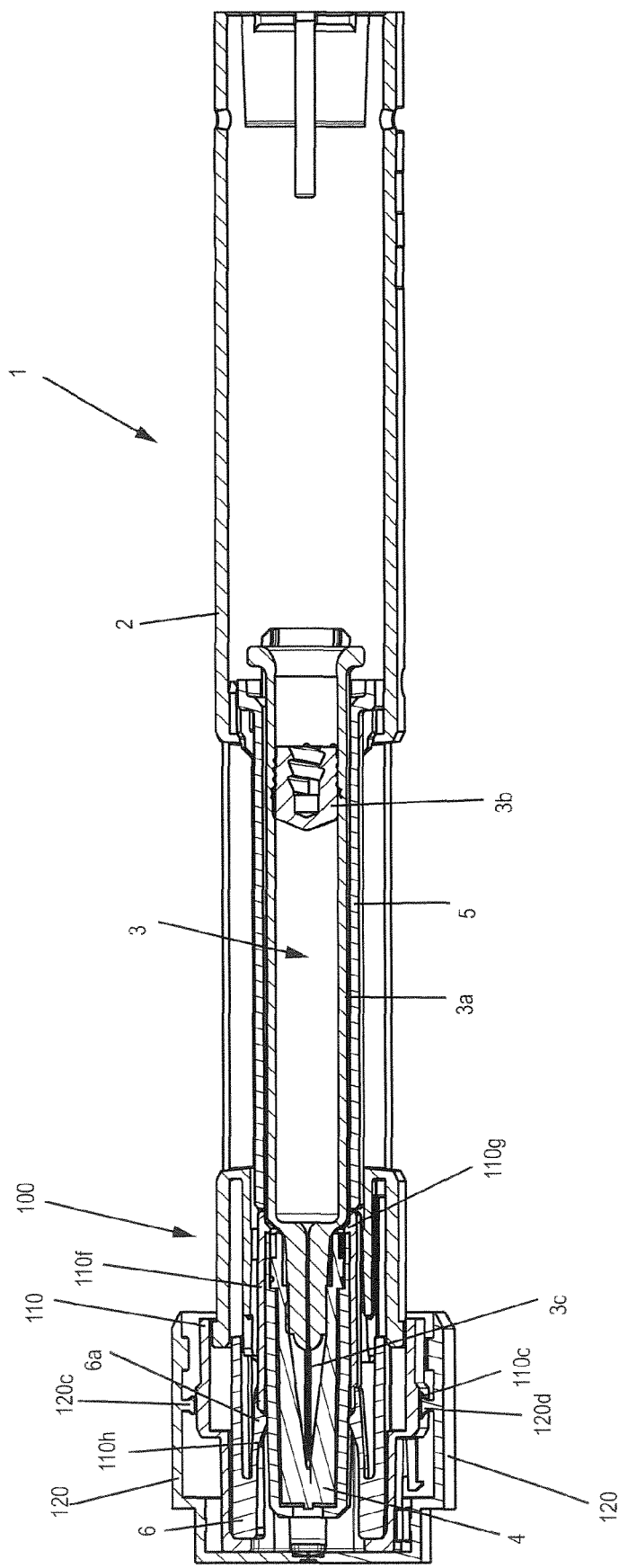
FIG. 3: longitudinal section through the autoinjector 1 and the detachable needle protection cap 100, where in this figure the syringe 3 with needle guard 4 and the syringe holder 5 are also shown.
Figure 5B:
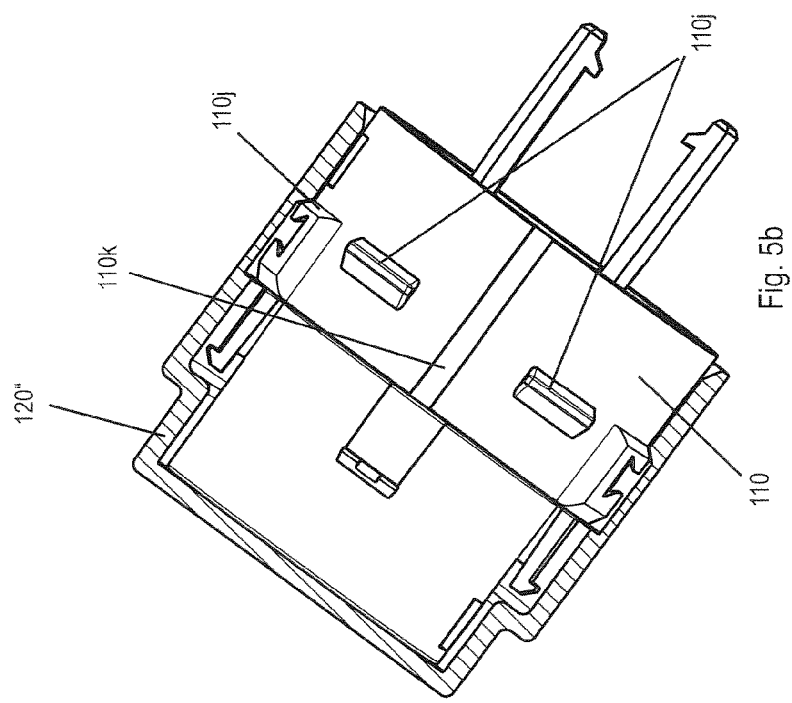
FIG. 5b: three-dimensional or perspective view with partial section of the further alternative shell part 120", placed on the housing 110. The shell part is shown cut.
Figure 5A:
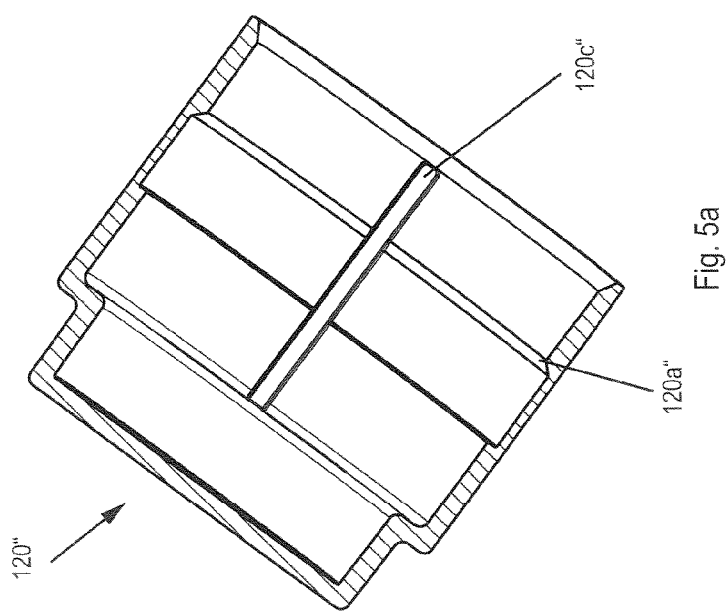
FIG. 5a: three-dimensional or perspective view of a further alternative embodiment of a shell part 120", where the shell part in this case is cut.

FIGS. 1 to 3 show a first embodiment of the invention. FIGS. 4a and 4b show an alternative embodiment of the shell parts; and FIGS. 5a and 5b show a simplified form of the shell with only one shell part.

FIG. 1 shows the autoinjector 1 together with the fitted detachable needle protection cap 100 in a three-dimensional view. Two shell parts 120 can be seen, which surround the housing 110 (not visible in FIG. 1) of the detachable needle protection cap 100. The housing 110 cannot be seen in this state by the user. The external shape of the shells may vary as already mentioned, and in fact, it is the purpose of the invention to enable a variation of the external shape (i.e. of the geometric external design of the detachable needle protection cap, specifically of the shell parts). The shell parts 120 depicted here serve purely as an example.

FIG. 2 shows an exploded view of the detachable needle protection cap together with the housing 2 and the needle protection sleeve 6 of the autoinjector 1. The other parts of the autoinjector 1 were left out, as indicated above. The housing 110 of the needle protection cap 100 comprises the recesses 110a into which the teeth 120b of the snap arms 120a can be engaged. The housing 110 also comprises the guide grooves 110b, into which the guide ribs 120c can be pushed when the shell part 120 is pushed on. One shell part 120 also comprises the blocking elements 120e. As mentioned, the shell parts 120 are individually fitted to the housing 110 when the detachable needle protection cap 100 is installed, by sliding the shell parts 120, 120 radially onto the housing 110, where the guide ribs 120c are pushed into the guide grooves 110b. Sliding-on of the shell parts 120, 120 is then complete when the teeth 120b engage in the recesses 110a of the housing 110 provided. Once an initial shell part 120 is installed, a second shell part 120 is pushed onto the opposite side of the housing 110, in a similar way to the first shell part 120. When the second shell part 120 snaps on to the housing 110, the blocking elements 120e of the one shell part 120 also engage with the rear side of the free end of the snap arm 120a in the area of the tooth 120b of the other shell part 120 and vice-versa. The blocking elements 120e prevent the snap arms 120a from being deflected radially outwards (not shown in the figures), thus preventing the snap joint from becoming detached.

FIG. 3 shows a longitudinal section through the autoinjector 1 and the detachable needle protection cap 100. This figure also shows the syringe 3 with glass body 3a, the movable plug 3b and the injection needle 3c, the needle guard 4 and the syringe holder 5 of the autoinjector 1. What can also be seen is the front part of the needle protection sleeve 6 of the autoinjector 1 with the snap arm 6a. Both shell parts 120 are installed onto the detachable needle protection cap 100. It can be seen in this figure that the guide grooves 110b have undercuts 110c. The guide ribs 120c also have a dovetail 120d, which engages with the undercuts. The function of this embodiment is to minimize the radial mobility of the shell parts 120 in the assembled state and thus to give the combination of housing 110 and shell parts 120 maximum stability. In principle, the user should not notice that the detachable needle protection cap 100 is made up of several parts. The detachable needle protection cap 100 is inserted axially into the autoinjector 1. In this case, the connection between the snap arm 6a of the needle protection sleeve 6 of the autoinjector 1 and the opening 110h of the housing 110 ensures that the detachable needle protection cap 100 remains on the autoinjector 1, where this connection is detachable. On the housing 110, two arms 110f protrude axially in the proximal direction. At their free end of the arms 110f, teeth 110g are arranged, which face radially inward. As can be seen in FIG. 3, the teeth 110g are located behind the proximal end of the needle guard 4. If the detachable needle protection cap 100 is now withdrawn distally from the autoinjector 1, then the proximal end of the needle guard 4 and the teeth 110g engage. If the detachable needle protection cap 100 is further moved distally, the teeth 110g carry the needle guard 4 with them and detach it from the syringe 3, thereby exposing the injection needle.

FIGS. 4a and 4b show the alternatively developed shell parts 120'. The design of the shell parts has been simplified. As with the shell parts of FIGS. 1 to 3, two shell parts are fitted to the housing 110 of the needle protection cap 100 (which is identical to that of FIGS. 1 to 3). Before pushing on the shell parts, two shell parts 120' are welded together along the weld seam which has been prepared with rib shapes and then pushed axially onto the housing 110 until the snap arms 110i are snap-fitted to the snap edge 120a'. In this case, when sliding the welded shell parts 120', the guide ribs 120c' are inserted into the guide grooves 110k provided. As in the examples of FIGS. 1 to 3, the guide grooves 110k also have undercuts (not shown) and the guide ribs 120c' are dovetailed (not shown) so that after the shell parts 120' are installed on the housing 110, any movement of the shell parts 120' in the radial direction relative to the housing 110 can be minimized. In the case of this embodiment too, the external geometry of the shells is merely an example because one aim of the invention is to allow different external shapes.

FIGS. 5a and 5b show a further simplification of the shell design by making two shell parts into one. Shell part 120" is pot shaped. Instead of two shell parts, only one shell is used in this embodiment, which is pushed onto the housing 110 in an axial direction, where the housing 110 is identical to the previous embodiments. The function of guide ribs 120c" and the guide grooves 100k is the same as in the example of FIGS. 4a and 4b. The shell part 120" is snapped over the snap edge 120a" of the shell part 120" and the snap teeth 110j of the housing 110.

Another benefit of the invention described is the design of the housing 110. As will be apparent to the person skilled in the art from the above description, the design of housing 110 described allows many different types of shell to be applied, without this entailing any change to the housing 110 design.

LIST OF REFERENCE NUMBERS 1 autoinjector
2 autoinjector housing
3 syringe
3a glass body
3b plug
3c injection needle or cannula
4 needle guard
5 syringe holder
6 needle protection sleeve of autoinjector
6a snap arm
100 detachable needle protection cap
110 housing
110a recess 110b guide groove
110c undercut
110d tooth
110f arm of detachable needle guard
110g tooth
110h opening
110i snap arm with tooth
110j axially directed snap tooth
110k guide groove with undercut
120 shell part
120a snap arm
120b tooth
120c guide rib
120d dovetail
120e blocking element
120' alternative embodiment of the shell part
120a' snap edge
120e' ribbed preparation for weld
120c' guide rib with dovetail
120" further alternative embodiment of the shell part
120a" snap edge
120c" guide rib with dovetail.

What is claimed is:

1. A process for producing a detachable needle protection cap for detaching a needle guard capable of being connected to an injection device, comprising the following steps:
providing a housing defining a longitudinal axis,
sliding and fastening an initial shell part to an external surface of the housing,
providing a further shell part by sliding and fastening the further shell part to the external surface of the housing,
permanently securing all slidably fastened shell parts by sliding and fastening a final shell part to the housing,
wherein the external surface of the housing comprises a plurality of holding points and a plurality of guide elements, and
wherein each of the initial shell part and the further shell part comprises at least one fixing element, a blocking element and at least guide counter-element arranged on an interior of a respective shell part.

2. The process according to claim 1, wherein the housing is configured to be detachably connected to a distal end of an injection device.

3. The process according to claim 1, wherein the initial shell part and the further shell part are configured to be attached to the external surface of the housing.

4. A process for producing a detachable needle protection cap for detaching a needle guard capable of being connected to an injection device, comprising the following steps:
providing a housing defining a longitudinal axis,
sliding and fastening an initial shell part to an external surface of the housing,
optionally providing a further shell part by sliding and fastening the optional further shell part to the external surface of the housing,
permanently securing all slidably fastened shell parts by sliding and fastening a final shell part to the housing,
wherein the external surface of the housing comprises a plurality of holding points and a plurality of guide elements, and
wherein each of the initial shell part and the optional further shell part comprises at least one fixing element, a blocking element and at least one guide counter-element arranged on an interior of a respective shell part.

5. The process according to claim 4, wherein the optional further shell part is provided, and wherein the initial shell part and the further shell part are attachable to the housing by engaging the respective at least one fixing element of the in a respective holding point of the plurality of holding points of the housing, and wherein the at least one fixing element of one of the initial shell part or the further shell part can be prevented from being released from an engagement with the respective holding point by a blocking element of the other of the initial shell part or the further shell part.

6. The process according to claim 4, wherein for fitting the initial shell part and the further shell part to the housing, the respective guide counter-elements are pushed into the guide elements.

7. The process according to claim 6,
wherein the plurality of guide elements of the housing are configured as one of a groove or a rib arranged perpendicular to the longitudinal axis of the housing, and wherein the at least one guide counter-element of each of the initial shell part and the further shell part is configured as the other of a groove or a rib, and
wherein the grooves comprise undercuts, and the ribs engage with the undercuts when the guide counter-elements are pushed into the guide elements, such that when the initial shell part and the further shell part are fitted to the housing, the initial shell part and the further shell part are held in a radial direction relative to the housing.

8. The process according to claim 1, wherein the plurality of holding points comprises a plurality of recesses on the external surface of the housing.

* * * * *